United States Patent
Mangat et al.

(10) Patent No.: US 9,433,608 B2
(45) Date of Patent: Sep. 6, 2016

(54) COMPOSITIONS AND METHOD FOR TREATMENT OF ISCHEMIC NEURONAL REPERFUSION INJURY

(71) Applicant: Howard University, Washington, DC (US)

(72) Inventors: Harpal S. Mangat, Potomac, MD (US); Pradeep K. Karla, Arlington, VA (US)

(73) Assignee: Howard University, Washington, DC (US)

( * ) Notice: Subject to any disclaimer, the term of this patent is extended or adjusted under 35 U.S.C. 154(b) by 0 days.

(21) Appl. No.: 14/273,370

(22) Filed: May 8, 2014

(65) Prior Publication Data

US 2014/0336183 A1 Nov. 13, 2014

Related U.S. Application Data

(60) Provisional application No. 61/821,123, filed on May 8, 2013.

(51) Int. Cl.

| | |
|---|---|
| A61K 31/5513 | (2006.01) |
| A61K 31/4178 | (2006.01) |
| C07D 405/12 | (2006.01) |
| A61K 45/06 | (2006.01) |
| A61K 38/05 | (2006.01) |
| A61K 31/13 | (2006.01) |
| A61K 31/5517 | (2006.01) |
| A61K 31/355 | (2006.01) |
| A61K 31/59 | (2006.01) |
| A61K 31/765 | (2006.01) |
| A61K 31/40 | (2006.01) |

(52) U.S. Cl.
CPC .......... *A61K 31/4178* (2013.01); *A61K 31/13* (2013.01); *A61K 31/355* (2013.01); *A61K 31/5513* (2013.01); *A61K 31/5517* (2013.01); *A61K 31/59* (2013.01); *A61K 31/765* (2013.01); *A61K 38/05* (2013.01); *A61K 45/06* (2013.01); *C07D 405/12* (2013.01); *A61K 31/40* (2013.01); *Y10T 428/2982* (2015.01)

(58) Field of Classification Search
None
See application file for complete search history.

(56) References Cited

U.S. PATENT DOCUMENTS

| | | | |
|---|---|---|---|
| 2,990,402 A | 6/1961 | Jack et al. | |
| 4,433,684 A | 2/1984 | Sarnoff et al. | |
| 6,462,066 B2 | 10/2002 | Mangat et al. | |
| 7,758,890 B2 | 7/2010 | Anderson et al. | |
| 2001/0053790 A1 | 12/2001 | Mangat et al. | |
| 2004/0122015 A1 | 6/2004 | Boykin et al. | |
| 2006/0030548 A1 | 2/2006 | Dong et al. | |
| 2006/0178354 A1 | 8/2006 | Lucas | |
| 2007/0265296 A1 | 11/2007 | Dalton et al. | |
| 2008/0090808 A1 | 4/2008 | Volvovitz | |

OTHER PUBLICATIONS

"Pharmacotherapy of Spasticity" by Noth in "Local-spinal Therapy of Spasticity" by Müller et al. (Eds.), Springer (Berlin Heidelberg) pp. 93-96 (1988).*
"Pluronic block copolymers as novel polymer therapeutics for drug and gene delivery" by Kabanov et al., J. Controlled Release 82, 189-212 (2002).*
PCT International Search Report and Written Opinion of the International Searching Authority dated Aug. 29, 2014 for International Application PCT/US2014/037359, 11 pages.
PCT International Search Report and Written Opinion of the International Searching Authority dated Sep. 4, 2014 for International Application PCT/US2014/037362, 17 pages.
Yasuhiro Tsume and Gordon L. Amidon, Selection of Suitable Prodrug Candidates for in vivo Studies via in vitro Studies; The Correlation of Prodrug Stability in Between Cell Culture Homogenates and Human Tissue Homogenates, Journal of Pharmacy & Pharmaceutical Sciences, 2012, vol. 15, No. 3, pp. 433-446.

* cited by examiner

*Primary Examiner* — Theodore R West
(74) *Attorney, Agent, or Firm* — Fitch, Even, Tabin & Flannery, LLP

(57) ABSTRACT

A method and composition for the treatment of ischemic neuronal reperfusion injury are provided. The composition may include at least a benzodiazepine class material. In another form, the composition may include at least two components selected from the group consisting of an antagonist of the type 3 ryanodine receptor, an NMDA blocker (antagonist), and a benzodiazepine class material which can be administered for ischemic neuronal reperfusion injury. In one form, all three components may be used.

6 Claims, No Drawings

COMPOSITIONS AND METHOD FOR TREATMENT OF ISCHEMIC NEURONAL REPERFUSION INJURY

CROSS-REFERENCE TO RELATED APPLICATIONS

This application claims benefit of U.S. Provisional Application Ser. No. 61/821,123, filed on May 8, 2013, which is hereby incorporated herein by reference in its entirety.

FIELD

This application is directed to the treatment of and prevention of ischemic neuronal injuries.

BACKGROUND

Interruption of the blood supply to neural tissues, such as the brain, can cause a complex series of biochemical changes which may result in neuronal cell damage. At the cellular level, it is generally understood that damage is mediated by opening of the N-methyl-D-aspartate (NMDA) channels in the membrane. Further, ischemia begins when the blood supply stops or is significantly slowed, and this ischemia phase may be followed by restoration of the blood supply during a reperfusion phase. It is understood that cellular damage may occur during both phases, though they occur through different mechanisms.

There are a complex series of events which contribute to cell death during ischemia/reperfusion. Six substances that accumulate during ischemia include excitatory amino acids, intracellular calcium, arachidonic and other free fatty acids, hypoxanthine, xanthine oxidase, and platelet activating factor.

Ischemia triggers at least three pathways deleterious to the cell. First, a lack of oxygen depletes energy stores (principally adenosine diphosphate known as ATP). This disrupts homeostatic mechanisms, most importantly the membrane pump mechanism that maintains intracellular calcium at low levels. The resulting rise in intracellular calcium, which occurs principally because of the opening of the N-methyl-D-aspartate (NMDA) channels in the membrane, increases release of glutamic acid, activates destructive proteases and lipases, and indirectly converts the enzyme xanthine dehydrogenase to the potentially harmful xanthine oxidase. Second, excitatory amino acids ("excitotoxins"), principally glutamic and aspartic acids, are released, activate calcium channels, further increase intracellular calcium through a positive feedback mechanism, and allow entry into the cell of excess water, sodium and chloride. Third, acidosis enhances destructive lipid peroxidation and the release of damaging free radicals.

Upon restoration of the blood supply, the reperfusion phase begins. An increased intracellular calcium level, a result of opened NMDA channels during ischemia, triggers a more destructive cascade. The initial calcium impulse causes a cascade which results in the release of intracellular calcium stores from the intravesicular calcium deposit. The release of intracellular calcium is mediated via the ryanodine receptor, principally the type 3 ryanodine receptor. The net result is a thirtyfold rise in intracellular calcium and cell death. Attempts have been made to reperfuse as soon as possible after the onset of ischemia, but it is important to note that the reperfusion itself causes the cascade, therefore the neurodestructive phases of ischemia and reperfusion are distinct.

Neurophysiologists view reperfusion injury as a cascade process that leads to excitotoxic cell death. The rise in intracellular calcium during reperfusion causes vasoconstriction of neighboring blood vessels. In addition, it causes the release of free oxygen radicals, in part from the action of xanthine oxidase. The net result is excitotoxic neuronal cell death.

Increased cytosolic $C_a^2+$ concentration contributes significantly to neuronal cell damage during ischemic reperfusion. U.S. Pat. No. 6,462,066 to Mangat et al. (which is incorporated herein as if fully rewritten) describes the above phenomena of ischemic injury and discusses the use of dantrolene to prevent or minimize neuronal cell damage that occurs during the reperfusion phase of an ischemic episode.

Dantrolene is an antagonist of the type 3 ryanodine receptor and is commonly given as the sodium salt (sodium dantrium), which is hydrated 1-[[[5-(4-nitrophenyl)-2-furanyl]methylene]amino]-2,4-imidazolidinedione sodium salt. Dantrolene is prescribed in the treatment of clinical spasticity resulting from upper motor neuron disorders such as spinal chord injury, cerebral palsy, stroke, or multiple sclerosis. Dantrolene is also effective in reversing the hypermetabolic process of malignant hyperthermia, a genetic disorder of skeletal muscle that is triggered by exposure to anesthetics and certain muscle relaxants.

The conflict in Iraq has produced an unprecedented number of traumatic brain injuries and has radically changed the way we treat trauma with the advent of Combat Surgical Hospitals on the frontline with injured troops arriving within an hour of injury. A patient might remain in the combat hospital for only six hours. The goal is lightning-swift, expert treatment, followed as quickly as possible by transfer to the military hospital in Landstuhl, Germany, for continued treatment.

American troops injured in Iraq have required limb amputations at twice the rate of past wars, and as many as 20 percent have suffered head and neck injuries that may require a lifetime of care. Accurate statistics are not yet available on recovery from this new round of battlefield brain (traumatic brain) injuries, an obstacle that frustrates combat surgeons. But judging by medical literature and surgeons' experience with their own patients some experts believe that three or four months from injury, 50 to 60 percent will be functional and doing things. In other words, these patients may be up and around, but with pretty significant disabilities, including paralysis. The remaining 40 percent to 50 percent of patients include those whom the surgeons send to Europe, and on to the United States, may have no prospect of regaining consciousness.

Preventing or minimizing neuronal cell damage that occurs during the reperfusion phase of an ischemic episode by virtue of a combat injury or other traumatic events which cause brain injuries or contusions with a non invasive administration of compounds which achieve higher and faster CNS penetration than dantrolene would be highly desirable and life saving.

Severe cerebral contusion is sometimes associated with early edema formation within 24-48 hours post-trauma, and this frequently results in progressive ICP (intracranial pressure) elevation, clinical deterioration and swelling. This swelling causes pressure on the brain squeezing it in the cranium (skull) and causing ischemic changes to the brain, often occluding fine blood supply to critical areas of the brain. Once steroids are on board to shrink the swelling there will be a secondary reperfusion injury as blood supply is re-established which contributes to further edema and neuronal cell death.

The mechanism of cell death for neurons is via the release of intracellular calcium. This leads to neuronal cell swelling/ death and edema. This pathway occurs both at initial ischemic insult and when the reperfusion injury occurs.

In another aspect, it has been recognized that certain nerve gasses based upon organophosphorus compounds, such as sarin, soman, tabun and cylcosarin (cyclohexyl methylphosphonofluoridate, a gas known as GF) cause ischemic injuries by generally the same mechanism as severe cerebral contusions. It has been found that the method of administration of dantrolene has not been successful in achieving effective neuroprotection against nerve gas attack.

In yet another aspect, other forms of ischemic brain injury may benefit from treatment. For example, stroke victims may also benefit from treatment of ischemic brain injury.

SUMMARY

It has been found that the use of a benzodiazepine class material may be appropriate for ischemic neuronal reperfusion injury.

In another form, it has been found that the use of at least two components selected from the group consisting of an antagonist of the type 3 ryanodine receptor, an NMDA blocker (antagonist), and a benzodiazepine class material may be appropriate for ischemic neuronal reperfusion injury. In one form, all three components may be used.

Suitable antagonists of the type 3 ryanodine receptor may include, but are not limited to, dantrolene, derivatives thereof and combinations thereof. Suitable examples of benzodiazepine class materials include, but are not limited to midazolam, diazepam, derivatives thereof and combinations thereof.

The antagonists of NMDA receptors (NMDA blockers) include a variety of suitable materials. For example, suitable compounds include memantine (3,5-dimethyladamantan-1-amine), such as having the general formula found below.

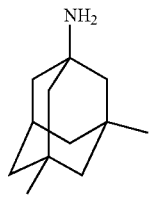

The antagonists of type 3 ryanodine receptors include dantrolene and/or a compound which is a combination of dantrolene and a residue of FMOC-valine (as shown in the general formulas I, II and III are set forth below), may also be used. It is believed that dantrolene and a residue of FMOC-valine provides a faster and higher CNS penetration than heretofore experienced with dantrolene.

general formula I

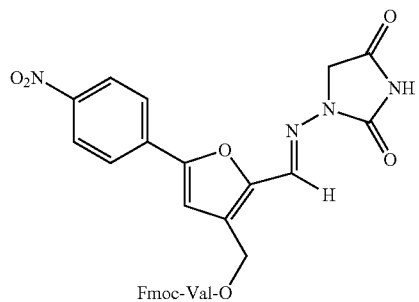

where FMOC-Val is the residue of FMOC-valine may be in the L or D form where FMOC-L-valine has the structure

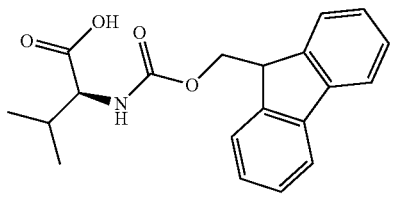 [SMILES: CC(C)[C@H](NC(=O)OCC1c2ccccc2-c2ccccc21)C(=O)O]

And where FMOC-D-valine has the structure

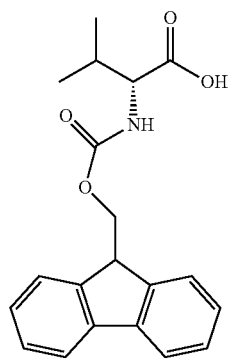 [SMILES: CC(C)[C@@H](NC(=O)OCC1c2ccccc2-c2ccccc21)C(=O)O]

The FMOC group may be removed as a "protective" group to provide general formula II

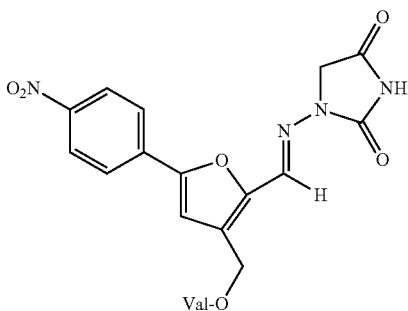

where "val" is a residue of

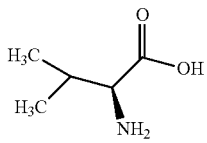

Third, a compound having the general formula III set forth below also may be used general formula III

[Structure: 4-nitrophenyl-furan with CH2-O-Val-Val substituent and hydantoin hydrazone]

Val-Val-O where val-val is a residue of

[Structure of Val-Val dipeptide with free NH2 and ketone]

The compound of general formula I may be made by the following synthesis.

[Scheme: 4-iodo-nitrobenzene + (n-Bu)3Sn-furan-CHO with THPO-CH2 substituent]
Catalyst, such as (Ph3P)2PdCl2
Solvent, such as DMF, 50° C., 4h

↓

[Structure: 4-nitrophenyl-furan-CHO with THPO-CH2]

+ [hydantoin hydrazide: H2N-N hydantoin]

H+, such as aq. HCl
Solvent, such as DMF

-continued

[Structure: 4-nitrophenyl-furan with THPO-CH2 and hydantoin hydrazone]

where THP is

[tetrahydropyran-2-yl structure]

and THPO CH2 is a residue of

[THP-O-R structure]

[Structure: hydantoin hydrazone product with THPO-CH2]

H+, such as aq HCl ↓

[Structure: hydantoin hydrazone with HO-CH2] + Fmoc-Valine [H3C, H3C, OH, Fmoc-NH]

Fmoc-Valine

Solvent, such as DMF | H+, such as HCl

↓

-continued

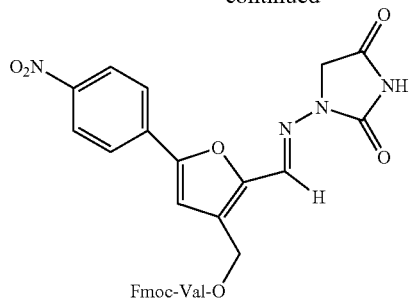

Fmoc-Val-O

DETAILED DESCRIPTION

Generally, the mechanism of neuronal injury that results in nerve cell death is excitotoxic. This menas that as the neuronal cell dies, it sets off mediators to neighboring cells resulting in an increase in cystolic calcium resulting in nerve cell death. In other words, there is the initial injury to the cell and then a cascading effect to other neighboring cells causing a worsening and/or spreading of the injury. It has unexpectedly been found that the initial injury as well as the spread of the injury may be treated with a combination of compounds.

It has been found that the use of a benzodiazepine class material may be appropriate for ischemic neuronal reperfusion injury. In one form, the benzodiazepine class material is selected from the group consisting of diazepam, midazolam, derivatives thereof and combinations thereof.

It has also been found that the use of at least two components selected from the group consisting of an antagonist of the type 3 ryanodine receptor, an NMDA blocker/antagonist and a benzodiazepine class material may be appropriate for ischemic neuronal reperfusion injury. These components may be provided in a single composition or may be provided as separate compositions. Further, these components may be administered at the same time or at different times.

Suitable antagonists of the type 3 ryanodine receptor may include, but are not limited to, dantrolene, val-dantrolene, val-val-dantrolene, derivatives thereof and combinations thereof. Suitable examples of NMDA blockers/antagonists include memantine, derivatives thereof and combinations thereof. Suitable examples of benzodiazepine class materials include, but are not limited to midazolam, diazepam, derivatives thereof and combinations thereof.

Memantine may be provided in the form found in the below general structure.

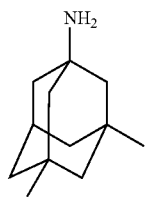

Dantrolene may be provided in the form found in the below general structure.

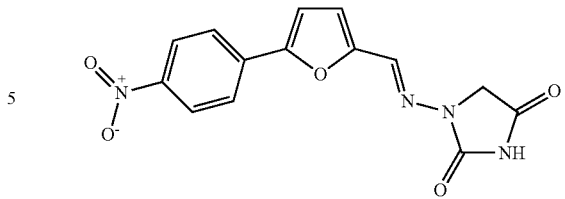

Dantrolene may also be provided as dantrolene sodium and related compounds. For example, it may be provided in the form of 1-[[5-(p-nitrophenyl)furfurylidene]amino]hydantoin sodium hydrate.

Memantine and dantrolene may also be prepared in other forms. For example, dantrolene may be provided in the form of compounds of general formulas I, II and/or III below. Memantine may also be administered in similar forms.

general formula I

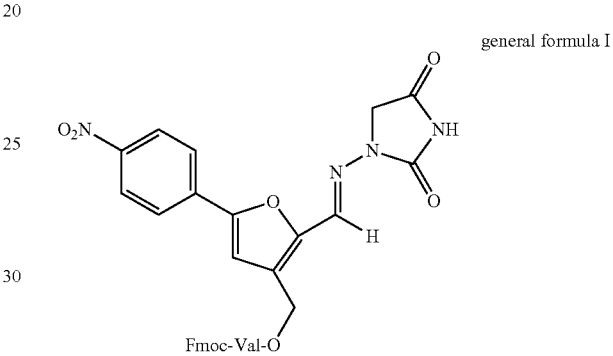

Fmoc-Val-O where FMOC-Val is the residue of FMOC-valine may be in the L or D form where FMOC-L-valine has the structure:

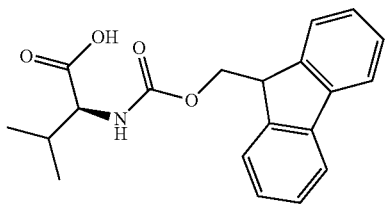 [SMILES: CC(C)[C@H](NC(=O)OCC1c2ccccc2-c2ccccc21)C(=O)O]

And where FMOC-D-valine has the structure:

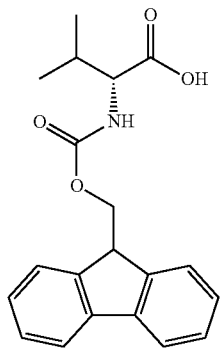 [SMILES: CC(C)[C@@H](NC(=O)OCC1c2ccccc2-c2ccccc21)C(=O)O]

The FMOC group may be removed as a "protective" group to provide general formula II

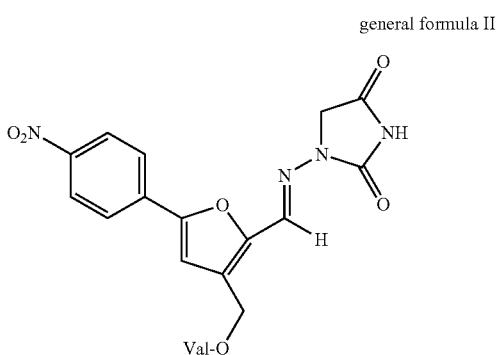

where "val" is a residue of

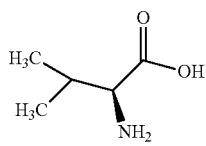

Third, a compound having the general formula III set forth below also may be used.

general formula III

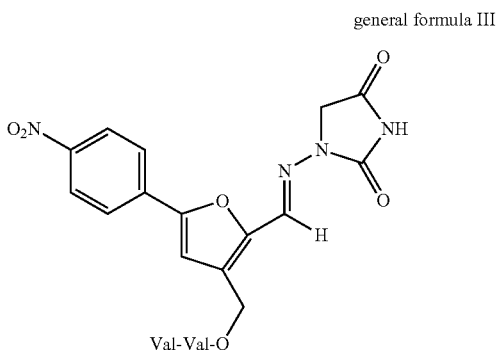

The at least one benzodiazepine class material may also take a variety of forms. For example, benzodiazepine class materials such as described in U.S. Pat. No. 4,226,771 may be used. In another form, diazepam (7-chloro-1,3-dihydro-1-methyl-5-phenyl-1,4-benzodiazepin-2(3H)-one) and/or midazolam (8-chloro-6-(2-fluorophenyl)-1-methyl-4H-imidazo[1,5a][1,4]benzodiazepine) may also be used such as found in the below structures.

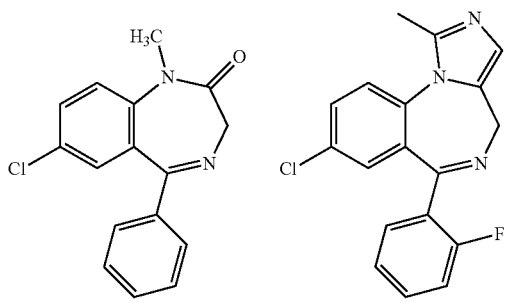 [SMILES: CN1C(=O)CN=C(c2ccccc2)c2cc(Cl)ccc21 ; Cc1ncc2n1-c1ccc(Cl)cc1C(c1ccccc1F)=NC2]

The compositions may also include pharmaceutically acceptable salts and can be administered alone or as an active ingredient in combination with pharmaceutically acceptable carriers, diluents, adjuvants and vehicles. For example, in one form, the compositions may be prepared in a nanoparticle emulsion form. The pharmaceutically acceptable carriers, diluents, adjuvants and vehicles, as well as implant carriers generally refer to inert, non-toxic solid or liquid fillers, diluents or encapsulating material not reacting with the active ingredients. The carrier can be a solvent or dispersing medium containing, for example, water, ethanol, polyol (for example glycerol, propylene, glycol, liquid polyethylene glycol, and the like), suitable mixtures thereof, and vegetable oils. For example, some of the active ingredients may be included with Vitamins D, E and/or pluronic acid as dantrolene is highly soluble in these materials. Similarly, excipients and other materials may be used, such as discussed in EP 2583670, which is incorporated by reference herein.

In one form, val-dantrolene is dissolved in Vitamin E until saturdation. In a separate container, dantrolene is dissolved with pluronic acid until saturation. The saturated Vitamin E and saturated pluronic acid components can then be mixed together with a suitable buffered saline solution by creating an emulsion suitable for administration.

In another form, val-dantrolene is dissolved in glycerin or Vitamin E until saturation. In a separate container, dantrolene is dissolved with polyethylene glycol/propylene glycol/pluronic acid until saturation. The two components can then be mixed together with a suitable buffered saline solution by creating an emulsion suitable for administration.

In one form, a rectal version of val-dantrolene that bypasses liver first pass metabolism may be used. According to one form, val-dantrolene is dissolved in glycerin or Vitamin E until saturation is reached. In a separate container dantrolene is dissolved with polyethylene glycol/propylene glycol/pluronic acid until saturation is reached. The saturated Vitamin E and satured pluronic acid is then mixed together and mixed with a suitable buffered normal saline solution creating an emulsion with a pH of 7.4.

In one form, the antagonist of the type 3 ryanodine receptor can be administered in a variety of manners. For example, the at least one antagonist of the type 3 ryanodine receptor can be administered such that it is not metabolized or exposed to digestion or the liver, it may be administered orally, subcutaneously, parenterally, intravenously, intranasally, intrathecally, sublingually, rectally, topically, and the like. It may also be provided in a zydis (fast buccal dissolving) form.

In one form, the NMDA blocker/antagonist can be administered in a variety of manners. For example, the NMDA blocker/antagonist can be administered such that it is not metabolized or exposed to digestion or the liver, it may be administered orally, subcutaneously, parenterally, intravenously, intranasally, intrathecally, sublingually, rectally, topically, and the like. It may also be provided in a zydis (fast buccal dissolving) form. It may also be provided in a zydis (fast buccal dissolving) form.

When administering the active ingredients, the compounds can be formulated in a unit dosage in a variety of forms such as a solution, suspension or emulsion. The pharmaceutical formulations also include sterile aqueous solutions or dispersions, and sterile powders for reconstitution into sterile solutions or dispersions.

According to one form, the type 3 ryanodine receptor and/or the NMDA blocker/antagonist may be administered through the lungs such as with a nebulizer (such as an ultrasonic and compressor nebulizer), gas mask, a gas masked with a nebulizer, a CPAP machine, an APAP machine and the like. In another form, the at least one antagonist of the type 3 ryanodine receptor can be particularly useful for administration through the lungs or intranasally because current dantrolene preparations contain sodium hydroxide which would have a deleterious effect on the lungs. In a particularly important aspect, the compounds are administered intranasally with a positive pulsating pressure with pulses occurring about every 5 seconds to 3 minutes.

The active ingredients, the type 3 ryanodine receptor, the NMDA blocker/antagonist, and the at least one benzodiazepine class material can be administered in a variety of different dosages and intervals as appropriate. The doses may be single doses or multiple doses over a period of several days. The treatment generally has a length dependent upon the length of the disease process, drug effectiveness and the patient being treated. In one form, 2-3 mg/kg of the type 3 ryanodine receptor is given every 2 hours for 6 hours and then every 8 hours. In one form, the NMDA blocker/antagonist may be administered in an amount of about 10-28 mg every 12 hours after an initial loading dose of 28 mg. In another form, 3 loading dosages are administered in the first 8 hours.

In one form, the at least one antagonist of the type 3 ryanodine receptor is provided in a dosage range of about 100 ng/kg to about 100 mg/kg per day. In one form, the dosage is provided in a range of about 1 mg/kg to about 10 mg/kg per day. It should be noted that lower dosages of the active ingredient may be provided while still being at least as effective relative to dantrolene being administered the same way with the same frequency. The NMDA blocker/antagonist may be administered in an amount of about 10-28 mg.

According to one form, the benzodiazepine class material may be administered in a dosage of about 2 mg to about 10 mg of diazepam and/or 0.02 mg/kg of midazolam. In one form, midazolam is administered in a dosage of about 0.005 mg/kg to about 0.05 mg/kg. Further, the benzodiazepine class material may be administered multiple times over the course of a day.

In yet another form, dantrolene, val-dantrolene, val-val-dantrolene and the like can be prepared in a powdered form. More specifically, the active ingredients can be formulated into optimally sized particles, such as 1-3 microns, through a liposomal or powder technique to permit the powder to be delivered efficiently into the lungs. Glass stabilization can be used for keeping the powders stable at room temperatures without the need for refrigeration. These powders can be in the form of blister packs.

The active ingredients may be formed in a variety of manners. In one form, the compound of general formula I may be made by the following synthesis.

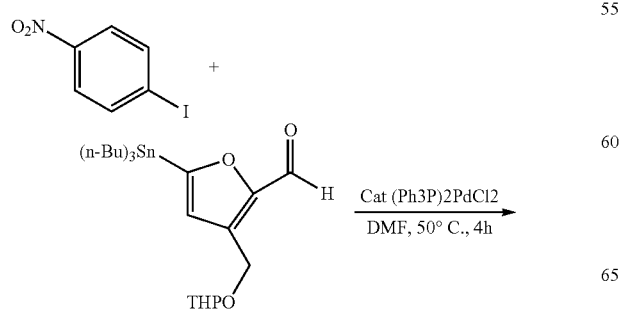

where THP is and THPO CH$_2$ is a residue of

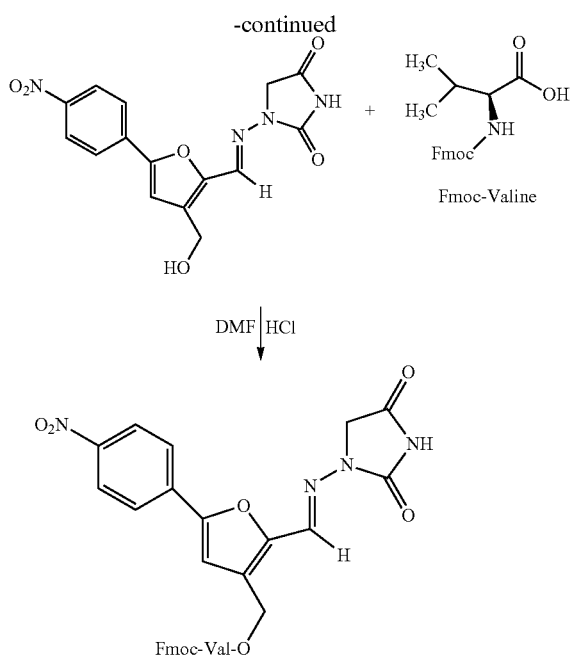

EXAMPLES

Example 1

An 89 year old man was brought by his family for lethargy and unsteady gait for 2 days after an episode of erratic behavior. Physical exam revealed no neurological deficit on the first day. A stat CT scan confirmed a 12 mm right basal ganglia infarct. MRI confirmed it to be an acute lacunar infarct. The Patient was given Memantine 10 mg twice daily and midazolam ordered. The family started the memantine but did not fill the midazolam script. Two days later the patient presents with a right sided leg weakness. Diazepam 2 mg twice a day was prescribed instead of midazolam. The patient was sent to physical therapy, the weakness resolved and there was no further expansion of the infarct or worsening of symptoms. After being on this treatment for 6 weeks it was stopped and the patient had returned to pre-stroke function.

Example 2

A 70 year old male presented with 3 week history of right side hemifield loss and a 3 day history of headache. MRI had confirmed a subacute temporal lobe infarct with encephalomalacia 4.6 cm craniocaudal, 3 cm traverse an 10 cm anterio posterior of the neighboring tissue. The patient had been on diazepam 10 mg daily and memantine 10 mg twice daily was added. The patient noted a clearing of fogginess but was unable to regain vision in the right hemifield.

When an infarct occurs in the brain, the sequence of events at a molecular level generally are as follows:
1) Opening of the NMDA channel to initiate a small calcium impulse.
2) Opening of the Ryanodine #3 receptor that causes efflux of stored calcium from the sarcoplasmic reticulum that leads to cell death and excitotoxicity.
3) Expansion of the excitotoxic damage to neighboring neuronal cells causing apoptosis and cell death.

In both of Examples 1 and 2, memantine was given to block step #1 and the midazolam/diazepam blocked step #3.

Example 3

A 78 year old woman presents 10 days after TIA (transient ischemic attack) symptoms. Initial CT scan of the head was reported as normal. She was seen by a Geriatric physician who noted she was developing aspiration pneumonia and dropping oxygen saturation. She was transferred her for intensive IV antibiotics.

The patient on arrival had a left sided arm contracture that had started six weeks earlier. She was placed on BIPAP with oxygen which she did not tolerate. Her mental function was poor and a decision was made to give palliative care of midazolam and glycopyrrolate on an initial prn basis.

On the first night 5 mg of midazolam was administered and 2 mg of glycopyrrolate along with 35% oxygen. The next day she was sitting talking to relatives, mentating better but could not swallow her own saliva. She started developing a right sided arm contracture with pupillary divergence and an ability to look out and to the left. She was placed on 5 mg of midazolam pump with 2 mg glycopyrrolate. The second night she could swallow her own saliva, but was drowsy from the midazolam. The third night the midazolam was stopped and restarted on the fourth night at a 2.5 mg pump along with 2 mg of glycopyrrolate The midazolam has been reduced to 2.5 mg daily (as the half-life doubles in patients older than 73) along with 2 mg glycopyrrolate. The midazolam like in nerve gas injury is preventing expansion of the penumbra of injury, whilst the glycopyrrolate is drying up the oral and pharyngeal secretions.

Applications

Midazolam and/or diazepam can be used alone at the onset of stroke or along with other neuroprotective agents such as dantrolene, memantine, derivatives thereof and combinations thereof.

Midazolam can be administered prior to bypass surgery alone or along with other neuroprotective agents such as dantrolene, memantine, derivatives thereof and combinations thereof.

Midazolam can be administered along with other neuroprotective agents such as dantrolene, memantine, derivatives thereof and combinations thereof in other applications.

In one form, the composition can be administered for a variety of ischemic injury related conditions, such as those described above. Further, the compositions can be administered for other ischemic-type conditions including, but not limited to, neuroprotecting against loss of neurological/cognitive function after coronary bypass surgery, stroke, dementia, and the like. The compositions can be used to protect both the dying cells in the umbria and prevent spread into the penumbra.

While the compositions and uses have been particularly described with specific reference to particular process and product embodiments, it will be appreciated that various alterations, modifications, and adaptations may be based on the present disclosure, and are intended to be within the spirit and scope of the invention as defined by the following claims.

What is claimed is:
1. A composition comprising:
an antagonist of a type 3 ryanodine receptor comprising at least one of val-dantrolene, val-val-dantrolene, and combinations thereof; and at least one additional material selected from the group consisting of an NMDA blocker, a benzodiazepine class material, derivatives thereof, and combinations thereof.

2. The composition of claim 1 wherein the benzodiazepine class material is selected from the group consisting of diazepam, midazolam, derivatives thereof and combinations thereof.

3. The composition of claim 1 wherein the NMDA blocker is selected from the group consisting of memantine, derivatives thereof and combinations thereof.

4. The composition of claim 1 further comprising at least one of Vitamin D, Vitamin E and a non-ionic surfactant.

5. A kit for treatment of neuronal reperfusion injury with ischemic neuropathy comprising:
   an antagonist of a type 3 ryanodine receptor comprising at least one of val-dantrolene, val-val-dantrolene, and combinations thereof; and
   at least one additional material selected from the group consisting of an NMDA blocker, a benzodiazepine class material, derivatives thereof, and combinations thereof.

6. The kit of claim 5 wherein both the NMDA blocker and the benzodiazepine class material are included.

* * * * *